United States Patent [19]

McDougal

[11] 3,950,588

[45] Apr. 13, 1976

[54] COATING OF SILANOL-REACTIVE SURFACES WITH DI-SILYL POLY(PERFLUOROOXYALKYLENES)

[75] Inventor: Janice E. McDougal, Shoreview, Minn.

[73] Assignee: Minnesota Mining and Manufacturing Company, St. Paul, Minn.

[22] Filed: Nov. 1, 1974

[21] Appl. No.: 520,209

[52] U.S. Cl. ...... 428/288; 260/46.5 R; 260/448.2 B; 260/448.8 R; 427/387; 428/422; 428/446
[51] Int. Cl.² .................... B32B 27/04; C07F 7/02
[58] Field of Search . 260/448.2 B, 448.8 R, 46.5 R; 428/422, 446; 427/387, 288

[56] References Cited
UNITED STATES PATENTS 3,646,085  2/1972  Bartlett ..................... 260/448.8 R
3,810,874  5/1974  Mitsch et al ..................... 260/485 F

*Primary Examiner*—George F. Lesmes
*Assistant Examiner*—R. V. Roche
*Attorney, Agent, or Firm*—Alexander, Sell, Steldt & DeLaHunt

[57] ABSTRACT

Substrates or articles having surfaces with silanol-reactive groups, e.g. glassware and ceramic cookware having hydroxylic surfaces, are coated with hydrolyzable di-silyl poly(perfluorooxyalkylene) compounds to provide said substrates or articles with a durable, oil and water repellent, abrasion resistant polysiloxane coating or film.

10 Claims, No Drawings

COATING OF SILANOL-REACTIVE SURFACES WITH DI-SILYL POLY(PERFLUOROOXYALKYLENES)

This invention relates to the treatment of substrates or articles having silanol-reactive surfaces, such as those of glassware, ceramic cookware, and the like, to render said surfaces oil and water repellent and abrasion resistant.

Though various perfluoroalkyl-containing silanes and siloxanes have been proposed or used heretofore in the treatment of glass and ceramic articles and the like to render the same oil and water repellent and abrasion resistant (e.g. see U.S. Pat. Nos. 3,423,234, 3,442,664, 3,666,538, and 3,772,346), prior art which appears to be most pertinent to the invention in the instant application is U.S. Pat. No. 3,646,085. However, the compounds disclosed in the latter patent as useful as oil and water repellents for glass substrates and the like have only a single terminal hydrolyzable silyl group, repeating oxyalkylene units which are exclusively —CF(CF$_3$)CF$_2$O—, and a terminal perfluoroalkyl group.

Briefly, this invention comprises coating a substrate having at its surface silanol-reactive groups, such as a glass or ceramic substrate, with a coating agent comprising a linear poly(perfluorooxyalkylene) compound terminated on each end with a trisubstituted-silyl group, the poly(perfluorooxyalkylene) portion of such compound comprising at least 80 percent by weight of randomly distributed repeating perfluorooxymethylene and perfluorooxyethylene units, and said substituted silyl groups being readily hydrolyzable to tri-hydroxy silyl groups, thereby providing said surface with a thin, durable, oil and water repellent, abrasion resistant coating or film facilitating the use and extending the life of the substrate, said coating being polysiloxane.

A class of di-silyl poly(perfluorooxyalkylene) compounds useful in coating surfaces having silanol-reactive group can be represented by the formula:

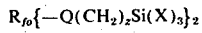

where R$_{fo}$ is a divalent, linear poly(perfluorooxyalkylene) backbone structure having a number average molecular weight, Mn, in the range of 500 to 10,000 or higher, and having the formula:

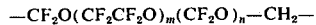

where (CF$_2$CF$_2$O) and (CF$_2$O) are randomly distributed oxyethylene and oxymethylene repeating units, respectively, where the subscripts m and n are integers whose ratio m/n is in the range of 0.2/1 to 5/1, preferably 0.5/1 to 2/1, X is a hydrolyzable group, such as halo (e.g. chloro, bromo), alkoxy (e.g. methoxy, ethoxy, isopropoxy, butoxy), or acyloxy (e.g. acetoxy), z is an integer of 2 to 11, and Q is a divalent organic linking group which is free of olefinic unsaturation and is stable (e.g. resistant to hydrolysis) under the conditions of said surface treatment. Representative examples of Q are —CON(R')— (where R' is hydrogen or an alkyl group of 1 to 4 carbon atoms), —CO—, —CO$_2$—, —COS—, —NR—, (where R' is hydrogen or an alkyl group of 1 to 4 carbon atoms), arylene having 6 to 15 carbon atoms (e.g. phenylene, —C$_6$H$_4$—), alkylene, oxaalkylene, and combinations thereof. Q is also free of silanol-reactive groups.

A preferred class of said di-silyl poly(perfluorooxyalkylene) compounds are those of the formula:

where R$_{fo}$, R', and z are as defined above in the case of formula I, and R'' is alkyl having 1 to 4 carbon atoms.

The above-described di-silyl poly(perfluorooxyalkylene) compounds are generally liquid at ambient temperature and have glass transition temperatures lower than −78°C. The compounds generally will have a number average molecular weight, Mn, in the range of 800 to 20,000 or higher. They are generally moderately soluble and stable in halogenated liquids, e.g. trichlorotrifluoroethane, and inert, completely fluorinated hydrocarbons, e.g. perfluorooctane, and various blends of aprotic polar liquids or hydrocarbons with such halogenated or fluorinated liquids.

Some of said di-silyl poly(perfluorooxyalkylene) compounds, and their preparation, are disclosed in U.S. Pat. No. 3,810,874 (e.g. compound 6 in Table I and Example XXVIII). One method of preparation is by the reaction of an alkyl di-ester of poly(perfluorooxyalkylene) di-acyl fluoride precursor with an aminoalkyltrialkoxysilane such as NH$_2$—(CH$_2$)$_2$NH(CH$_2$)$_3$Si(OCH$_3$)$_3$ or NH$_2$(CH$_2$)$_3$Si(OC$_2$H$_5$)$_3$. Another method is by the reaction of poly(perfluorooxyalkylene) di-acyl fluoride precursor with aminoalkyltrialkoxysilane. Another method is by reaction of a di-terminally ethylenically unsaturated derivative of poly(perfluorooxyalkylene) di-acyl fluoride precursor, such as the di-alkenylamide, -vinyltriazene, -acrylate, or -vinyl derivatives, with amino-, hydroxy-, or mercapto-substituted silane. Still another method is the reaction of di-amino, -hydroxyl, or -mecapto derivative of the poly(perfluorooxyalkylene) di-acyl fluoride precursor with isocyanato-substituted silane. The above described reactions are disclosed in U.S. Pat. No. 3,646,085 and said U.S. Pat. No. 3,810,874, the latter disclosing said poly(perfluorooxyalkylene) di-acyl fluoride and derivatives and their preparation. The poly(perfluorooxyalkylene) precursors are usually obtained in the form of mixtures of compound having R$_{fo}$ backbones of varying molecular weights and thus the di-silyl derivatives as used in this invention will correspondingly be in the form of mixtures thereof.

Representatives di-silyl poly(perfluorooxyalkylene) compounds useful in this invention include those of the following formula:

     IV

     V

     VI

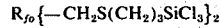     VII

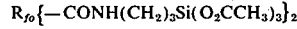     VIII

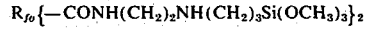     IX

The di-silyl poly(perfluorooxyalkylene) treating agents of this invention can be applied to surfaces having silanol-reactive groups, such as hydroxyl, carboxyl and amino, particularly siliceous substrates or articles, such as glass, ceramic, and lithic substrates, cellulosic substrates, such as films and fibers, proteinaceous substrates, such as wool and leather, and the like. Flat glass or window glass, such as used for automobile windshields and buildings and the like, glassware, such as used in laboratories or in the home, and ceramic substrates, such as bathroom tiles, sparkplugs, cookware and cooktops, can be treated in accordance with this invention.

Treatment of said substrates results in rendering the treated surfaces less retentive of soil and more readily cleaned due to the oil and water repellent nature of the treated surfaces. Also the useful life of the treated substrate, particularly treated glassware, is extended because of the abrasion or scratch resistance of the treated substrate. These desirable properties are maintained despite extended exposure or use and repeated cleanings because of the surprisingly high degree of durability of the treated surface as compared to that heretofore obtainable or known.

The coating agent used in this invention can consist of the di-silyl poly(perfluorooxyalkylene) compound per se — that is, the compound can be used neat — or, preferably for purposes of efficiency and economics, can be in the form of a dilute solution or dispersion in a volatile liquid medium such as aprotic compounds, e.g. ketones such as acetone or methyl ethyl ketone, esters, e.g. ethyl acetate, hydrocarbons, e.g. pentane and toluene, ethers, e.g. diethyl ether, halogenated hydrocarbons, e.g. trichlorotrifluoroethane, completely fluorinated hydrocarbons, e.g. perfluorooctane, and various blends of these materials. The concentration of the di-silyl poly(perfluorooxyalkylene) compound in the solution or dispersion can vary, depending upon the particular materials used and the application technique, but generally the concentration will be 0.05 to 50 weight percent or higher.

Methods of application of the coating agent to the substrate include brushing, spraying, dipping, rolling, spreading, and the like. Following application, the treated substrate can be dried at ambient or elevated temperature, e.g. at 20° to 100°c. One particularly convenient method of application will be that of wiping the substrate with a woven or non-woven, inert fabric or carrier impregnated or containing the coating agent, such carrier being relatively porous and flexible. The impregnated carrier or wipe can be sealed in a moisture-proof package until it is ready to be used.

The amount of di-silyl poly)perfluorooxyalkylene) to be coated on the substrate will be that amount sufficient to produce a coating which is water and oil repellent, such a coating having at 20°C a contact angle with distilled water of at least 80°, and a contact angle with n-hexadecane of at least 40°. This coating can be extremely thin, e.g. 1 to 50 molecular layers, though in practice a useful coating may be thicker. Said coating also is durable and abrasion and scratch resistant.

Upon contact of the substrate with the di-silyl poly(-perfluorooxyalkylene), in the presence of adventitious moisture, the compound becomes firmly bonded to the substrate and forms a cross-linked, relatively transparent polysiloxane film. In order to promote such reaction, the substrate to be coated should be relatively dry, that is, though the surface of the substrate to be coated normally will have adsorbed water, the surface should be free of water as a separate phase. And care should also be taken to maintain the coating agent in relatively anhydrous conditions prior to use.

The polysiloxane can be considered as being made of repeating units of the formula:

   x where Q, $R_{fo}$, and $z$ are as defined in formula I. In the polysiloxane structure, the silicon atoms of the repeating units are generally co-valently bonded to oxygen atoms, some of which in turn are bonded to atoms in the substrate surface and others of which are bonded to silicon atoms of adjacent repeating units.

In this application, the term "poly(perfluorooxyalkylene)" is meant to be synonymous to "poly(pefluoroalkylene oxide," the latter term being employed in the disclosure of said U.S. Pat. No. 3,810,874 which, as mentioned, discloses disilyl poly(perfluorooxyalkylene) compounds, and their preparation, useful as coating agents in this invention. The term "silanol" as used herein refers to the

group.

The formation of the latter group from the terminal hydrolyzable silyl groups of the poly(perfluorooxyalkylene) compound will require, as is known in the art, hydrolyzing conditions, viz. the presence of at least a stoichiometric amount of water, which amount is readily available from adventitious moisture in the ambient atmosphere at a relative humidity, for example, of 25% or higher.

Objects and advantages of this invention are illustrated in the following examples but the various materials and amounts recited therein, as well as conditions and other details, should not be construed to unduly limit this invention.

EXAMPLE 1

In a 100 ml glass flask, equipped with a magnetic stirrer and dropping funnel and maintained under a nitrogen atmosphere, was charged 50 g of the diester $CH_3O_2C—CF_2O(CF_2CF_2O)_m(CF_2O)_nCF_2—CO_2CH_3$ ($\bar{M}n = 2000$, m/n = 0.7). Over a period of 15 min., 11.0 g of the silane $H_2N(CH_2)_3Si(OC_2H_5)_3$ (sold as "A-1100 Silane") was added and the resulting solution stirred at room temperature for 16 hrs. The resulting reacted solution was then subjected to reduced pressure (1 Torr) at 50°C to remove the methanol liberated during the reaction. As confirmed by infrared analysis, the resulting di-silyl poly(perfluorooxyalkylene) product had the structure shown in formula V. Soda lime glass microscope slides coated with this product were found at about 20°C to have an average contact angle with distilled water of 105° and with n-hexadecane of 60°C.

EXAMPLE 2

A di-silyl poly(perfluorooxyalkylene) product was prepared in the manner similar to that described in Example 1 except that the diester precursor had an $\bar{M}n$ of 4000 and the amount of the silane used was 5.5 g. Infrared analysis of the resulting di-silyl poly(perfluorooxyalkylene) product confirmed it as having the structure of said formula V.

EXAMPLE 3

A di-silyl poly(perfluorooxyalkylene) product was prepared in the manner described in Example 1 except that 10 g of the diester precursor was used and 2.2 g of $NH_2CH_2CH_2NH(CH_2)_3Si(OCH_3)_3$ (sold as "A-1120 Silane") was used as the silane reactant. Infrared analysis confirmed the di-silyl poly(perfluorooxyalkylene) product as having the structure of formula IX.

EXAMPLE 4

A 1% solution (wt/vol) of the di-silyl poly(perfluorooxyalkylene) product of Example 1 was prepared in a 50/50 solvent blend of 1,1,2-trichloro-1,2,2-trifluoroethane ("Freon 113") and a mixture of saturated fully fluorinated inert fluoroaliphatic compounds boiling at about 100°C. Soda lime glass microscope slides were spread with the 1% solution, the excess solution drained from the slides after 45 seconds, the treated slides dried for 5 min. at about 20°C, and the dried slides rinsed with Freon 113 and buffed with a paper towel. The repellency of the treated surface to various liquids was determined by contact angle measurement, the results being summarized in the following table:

| Test | Test liquid | Contact angle on untreated surface | Contact angle on treated surface |
|---|---|---|---|
| 1 | Distilled $H_2O$ | 11° | 98° |
| 2 | 2-Ethyl-1-hexanol | (too low to measure) | 29° |
| 3 | Motor Oil ("Penzoil" 10W-20W-30) | 15° | 57° |
| 4 | Glycerol | 23° | 93° |
| 5 | Aqueous NaCl (50% sat'd) | 13° | 103° |
| 6 | Aqueous $CaCl_2$ (50% sat'd) | 20° | 103° |
| 7 | Corn syrup ("Karo") | 47° | 105° |
| 8 | Vegetable oil ("Crisco") | 15° | 62° |

The relatively higher contact angle of the treated surface shows a high degree of repellency to liquids.

EXAMPLE 5

A wipe was prepared by saturating a non-woven web of polyester fibers with a 10% solution (wt/vol) of the di-silyl poly(perfluorooxyalkylene) product of Example 1 in a 50/50 solvent blend of n-pentane and the mixture of fluroaliphatic compounds described in Example 4, and the resulting impregnated web allowed to dry at ambient temperature to remove most of the solvent. Soda lime glass microscope slides were then rubbed with the wipe, the treated surfaces allowed to dry for about 30 min. at ambient temperature, and the dried surfaces buffed with a paper towel. The contact angles of distilled water on the treated surfaces averaged 96°, demonstrating again the high degree of water repellency of the treated surface.

EXAMPLE 6

Vertical glass plates were spray coated with a 0.25% (wt/vol) solution of the di-silyl poly(perfluorooxyalkylene) product of Example 1 in Freon 113 and the treated surfaces buffed with paper towel. The treated surfaces were found to have an average contact angle of 106° with distilled water whereas untreated glass plates had a contact angle of only 35° with distilled water, again demonstrating the high degree of water repellency of the treated surface. After 300 hours under "Weather-O-Meter" test conditions (equivalent to 12 months exposure to actual atmospheric conditions), the average contact angles of the treated surfaces were 94° with distilled water, demonstrating the durability of the treated surfaces.

EXAMPLE 7

Vertical glass plates were spray coated and dried in the same manner described in Example 6. The resulting treated surfaces were found to have an average contact angle of 108° with distilled water. After 200 cycles of abrasion of the treated surfaces with a "Tabor Abrader," having a rubber wheel covered with cheesecloth and under a 1000 g load, the treated surfaces were found to have essentially the same contact angle with distilled water, demonstrating the abrasion resistance of the treated surfaces. When the other similarly treated glass plates were subjected to the abrasive action of a "Tabor Abrader" using an abrasive wheel (CS-10F) under a 1000 g load, it was found that only after 700 cycles did the treated surface have a contact angle with distilled water that was essentially the same as that of the untreated surface, by which time the treated glass surface was found to be scratched.

EXAMPLE 8

Soda lime microscope glass slides were treated with coating agent in the manner described in Example 4 and the treated slides tested to determine the durability of the treated surface after repeated washing in hot detergent solution. Each washing cycle consisted of
1. Immersing the treated glass slides for 1 min. at 80°C in a 1% detergent solution of "Alconox";
2. Rinsing with running water;
3. Drying with acetone; and
4. Buffing the treated surface with paper towel. The contact angle of distilled water on the treated surfaces was periodically determined. Results are set forth in the following table together with, for purposes of comparison, the results obtained by treating glass slides with "Rain.X" and "Total Finish," commercial automotive polysiloxane glass treating agents. The Rain.X was applied to the glass slides with cheesecloth dampened with the Rain.X coating agent and the slides then dried for 1 min. and buffed with paper towel, according to the directions supplied by the manufacturer. The Total Finish was applied in the same manner except that drying was accomplished over night, according to the manufacturer's directions.

| | Contact angle with distilled water | | |
|---|---|---|---|
| Cycles | 1% soln. of di-silyl compound | Rain-X | Total Finish |
| 0 | 106° | 92° | 96° |
| 5 | 106° | 68° | 93° |
| 10 | 108° | 45° | 89° |
| 15 | 105° | — | 71° |
| 25 | 104° | — | — |
| 50 | 100° | — | — |

The data of the above table demonstrate the superior durability of the di-silyl compound coating in that the contact angle remained substantially constant for at least the first 25 cycles.

EXAMPLE 9

Soda lime microscope glass slides were coated as in Example 4. Following the evaporation of the solvent, the slides were rinsed in Freon 113 and allowed to air dry without buffing. The thus prepared slides were then subjected to the same detergent wash durability test described in Example 8 except that, following the treatment with acetone, the slides were not buffed. As in Example 8, the contact angle of distilled water was determined periodically. For purposes of comparison, other glass slides were treated with three commercial products (viz. "Dri-Film" SC-87, "Siliclad," and "Glasskote") sold for the treatment of laboratory glassware. In using these commercial products, solutions were made following the manufacturer's directions. The "Dri-Film" SC-87 was coated from a 10% solution of Dri-Film in decane and the slides then dried for 30 min. at 100°C. The "Siliclad" was made into a 1% solution in warm water, the slides dipped in the solution for 10 seconds, the treated slides rinsed under running water and then oven-dried for 10 min. at 100°C. The "Glasskote" was sprayed on the slides and the treated slides then rinsed under running water and oven-dried for 10 min. at 100°C. These three sets of comparison slides were then subjected to the same detergent wash durability test and the contact angles of distilled water were likewise determined periodically. Results of these tests are set forth in the following table:

| Cycles | Contact angle with distilled water | | | |
|---|---|---|---|---|
| | 1% soln. of di-silyl compound | Dri-Film SC-87 | Glasskote | Siliclad |
| 0 | 112° | 87° | 57° | 75° |
| 5 | 107° | 90° | 22° | 53° |
| 10 | 105° | 85° | — | 45° |
| 15 | 101° | 80° | — | — |
| 20 | 103° | 73° | — | — |
| 25 | 100° | — | — | — |
| 50 | 100° | — | — | — |

These data show that the water repellency of the di-silyl compound coating was initially, and even after 50 cycles, greater than that of the other coatings initially.

EXAMPLE 10

Soda lime glass microscope slides were coated in a manner similar to Example 4 with a 1% (wt/vol) Freon 113 solution of the di-silyl poly(perfluorooxyalkylene) product of Example 1. Contact angles of distilled water on the treated surfaces averaged 100°. Chemical resistance was then tested in two different manners: in one manner, the given chemical was wiped on the treated surface, the surface rinsed under running water, wiped dry, the chemical reapplied, again rinsed and dried, and this procedure repeated for 25 cycles; in the other manner, the treated slides were soaked in the chemical for 164 hours and then rinsed under running water and dried. Of 40 representative chemicals tested (acids, anhydrides, aliphatic and aromatic hydrocarbons, alcohols, amines, esters, ethers, ketones, chlorinated and polymer solvents, inorganic bases, peroxides, halogens, salt solutions), only hydrofluoric acid (49%), aqua regia, aqueous sodium hydroxide (50%), and aqueous ferric chloride (25%) caused significant reduction in contact angle of distilled water.

EXAMPLE 11

Wipes prepared as described in Example 5 were used to treat a number of "Pyrex" glass beakers. When only the lips of the beakers were treated with the wipe, and water was poured from the beakers and the beakers set upright, no drips ran down the outside of the beakers from the treated lips. Additionally, when the whole interior surface of the beakers was treated with the wipe, and water was poured out of the beakers, no clinging of liquid was observed on the interior wall or bottom of the beakers. In contrast, untreated beakers were found to have drips running down the outsides of the beakers and significant water clinging to the insides of the beakers. Similar differences were noted with a variety of other liquids.

A glass buret was treated with a 1% Freon 113 solution of the di-silyl poly(perfluorooxyalkylene) product of Example 1 by filling the buret with the solution, draining the buret after 1 min., and rinsing the buret with Freon 113. The resulting treated buret no longer exhibited a meniscus when filled with water and the treated buret could be read accurately immediately after a portion of the liquid was removed therefrom without the necessity of waiting for the liquid to drain.

EXAMPLE 12

A 1% Freon 113 solution of di-silyl poly(perfluorooxyalkylene) product of Example 1 was used in the treatment of glazed ceramic bathroom tiles. From the manner in which water beaded up on the treated surfaces of the tiles, the contact angle was estimated to be greater than 90°, demonstrating the repellent nature of the treated surface. This degree of repellency was retained through 50 hot detergent cycles run as described in Example 8.

EXAMPLE 13

"Pyrex" glass cake pans and a "Corningware" ceramic casserole dish were wiped with a 1% Freon 113 solution of the di-silyl poly(perfluorooxyalkylene) product of Example 1. The treated bakeware was used repeatedly to bake cakes and casseroles and after each use was found to readily release baked food residue when washed, as compared to the results obtained when untreated bakeware was used.

One-half of a commercial ceramic cooking surface was treated with the wipe described in Example 5. Food was deliberately burned on the cooking surface and it was found that the treated portion of the cooking surface was much easier to clean than the untreated portion of the surface, the treated portion requiring less than one-half of the number of applications of a commercial cleanser to remove the burned-on stains.

The lip of a "Pyroceram" cream pitcher was treated with the above-described wipe and when the contents of the pitcher were poured and the pitcher placed upright, no drips formed along the exterior of the pitcher.

EXAMPLE 14

One-half of the outside of the clean windshield of an automobile was spray coated with the 1% solution of di-silyl poly(perfluorooxyalkylene) product of Example 4, the coated windshield allowed to dry at ambient temperature for about 10 min. and then buffed to transparency with paper towels wet with Freon 113. Over a period of six months of normal use of the automobile, notably superior visibility in rain through the treated portion of the windshield was experienced. The treated portion of the windshield also stayed cleaner and released frost easier, as compared to the untreated portion.

EXAMPLE 15

The outside of a number of cleaned windows of a house were spray coated with the 1% coating solution described in Example 4. The coated windows were allowed to dry in air at ambient temperature for several minutes and then buffed to transparency with paper towel. The coated windows were examined over the course of several weeks and were found to be considerably cleaner than untreated windows of the house.

EXAMPLE 16

One lens of each of a number of pairs of eyeglasses was treated with a wipe of the type described in Example 5. The treated lens of each pair was easier to maintain in a clean condition than the untreated lens even after two months of use.

Various modifications and alterations of this invention will become apparent to those skilled in the art without departing from the scope and spirit of this invention.

What is claimed is:

1. A porous, woven or non-woven, inert, resilient carrier impregnated with a linear poly(perfluorooxyalkylene) compound terminated on each end with a trisubstituted-silyl group hydrolyzable to a tri-hydroxysilyl group, said compound having the formula:

$$R_{fo}\{-Q(CH_2)_zSi(X)_3\}_2$$

where $R_{fo}$ is a divalent, linear poly(perfluorooxyalkylene) backbone structure having a number average molecular weight in the range of 500 to 10,000 and has the formula:

$$-CF_2O(CF_2CF_2O)_m(CF_2O)_n-CF_2-$$

where $(CF_2CF_2O)$ and $(CF_2O)$ are randomly distributed oxyethylene and oxymethylene repeating units, respectively, where the subscripts m and n are integers whose ratio m/n is in the range of 0.2/1 to 5/1, X is a hydrolyzable group selected from the group consisting of halo, alkoxy, and acyloxy, z is an integer of 2 to 11, and Q is a divalent organic linking group which is free of olefinic unsaturation and silanol-reactive groups.

2. The article of claim 1, wherein said compound has at least 40 wt % carbon-bonded fluorine in the form of perfluorooxyalkylene.

3. The article of claim 1, wherein Q is $-CON(R')-$, where R' is hydrogen or an alkyl group of 1 to 4 carbon atoms, and X is an alkoxy group having 1 to 4 carbon atoms.

4. The article of claim 1, wherein said carrier comprises a non-woven web of polyester fibers.

5. The article of claim 1, wherein said compound has the formula $$R_{fo}\{-CONH(CH_2)_3Si(OCH_3)_3\}_2$$

where $R_{fo}$ is as defined in claim 1.

6. The article of claim 1, wherein said compound has the formula $$R_{fo}\{-CONH(CH_2)_3Si(OC_2H_5)_3\}_2$$

where $R_{fo}$ is as defined in claim 1.

7. The article of claim 1, wherein said compound has the formula $$R_{fo}\{-CH_2NHCOS(CH_2)_3Si(OCH(CH_3)_2)_3\}_2$$

where $R_{fo}$ is as defined in claim 1.

8. The article of claim 1, wherein said compound has the formula $$R_{fo}\{-CH_2S(CH_2)_3SiCl_3\}_2$$

where $R_{fo}$ is as defined in claim 1.

9. The article of claim 1, wherein said compound has the formula $$R_{fo}\{-CONH(CH_2)_3Si(O_2CCH_3)_3\}_2$$

where $R_{fo}$ is as defined in claim 1.

10. The article of claim 1, wherein said compound has the formula $$R_{fo}\{-CONH(CH_2)_2NH(CH_2)_3Si(OCH_3)_3\}_2$$

where $R_{fo}$ is as defined in claim 1.

* * * * *

UNITED STATES PATENT AND TRADEMARK OFFICE
CERTIFICATE OF CORRECTION

PATENT NO. : 3,950,588
DATED : April 13, 1976
INVENTOR(S) : Janice E. McDougal

It is certified that error appears in the above-identified patent and that said Letters Patent are hereby corrected as shown below:

Column 1, line 46, "Mn" should read -- $\overline{Mn}$ --;

Column 2, line 47, "Representatives" should read -- Representative --;

Column 2, line 49, "formula" should read -- formulas --;

Column 6, lines 32-46, "The contact angle...the manufacturer's directions." should not be read as part of step "4" on line 32 and should not be indented.

Signed and Sealed this

Thirty-first Day of August 1976

[SEAL]

Attest:

RUTH C. MASON
*Attesting Officer*

C. MARSHALL DANN
*Commissioner of Patents and Trademarks*